United States Patent
Dale et al.

(10) Patent No.: US 11,772,996 B2
(45) Date of Patent: *Oct. 3, 2023

(54) PROCESS FOR TREATING CONTAMINATED WATER

(71) Applicant: Neozyme International, Inc., Costa Mesa, CA (US)

(72) Inventors: Parker Dale, Newport Beach, CA (US); Parker David Dale, Newport Beach, CA (US)

(73) Assignee: Neozyme International, Inc., Costa Mesa, CA (US)

( * ) Notice: Subject to any disclaimer, the term of this patent is extended or adjusted under 35 U.S.C. 154(b) by 804 days.

This patent is subject to a terminal disclaimer.

(21) Appl. No.: 16/729,243

(22) Filed: Dec. 27, 2019

(65) Prior Publication Data

US 2020/0140304 A1     May 7, 2020

Related U.S. Application Data

(60) Continuation of application No. 15/444,093, filed on Feb. 27, 2017, now Pat. No. 10,683,222, which is a division of application No. 14/404,917, filed as application No. PCT/US2013/000140 on May 24, 2013, now Pat. No. 9,617,178.

(60) Provisional application No. 61/689,077, filed on May 29, 2012.

(51) Int. Cl.
| | | |
|---|---|---|
| *C02F 3/34* | (2023.01) | |
| *C12N 1/18* | (2006.01) | |
| *C12N 1/16* | (2006.01) | |
| *C02F 3/02* | (2023.01) | |
| *C02F 3/28* | (2023.01) | |
| *A01N 63/32* | (2020.01) | |
| *C02F 11/04* | (2006.01) | |
| *C12P 5/02* | (2006.01) | |
| *C02F 101/32* | (2006.01) | |
| *C02F 103/00* | (2006.01) | |
| *A01N 37/44* | (2006.01) | |

(52) U.S. Cl.
CPC .............. *C02F 3/347* (2013.01); *A01N 63/32* (2020.01); *C02F 3/02* (2013.01); *C02F 3/28* (2013.01); *C02F 11/04* (2013.01); *C12N 1/16* (2013.01); *C12N 1/18* (2013.01); *C12P 5/023* (2013.01); *A01N 37/44* (2013.01); *C02F 3/282* (2013.01); *C02F 3/342* (2013.01); *C02F 2101/32* (2013.01); *C02F 2103/007* (2013.01); *C02F 2301/106* (2013.01); *C02F 2303/02* (2013.01); *C02F 2303/10* (2013.01); *C02F 2305/04* (2013.01); *C12N 2500/74* (2013.01); *Y02E 50/30* (2013.01); *Y02W 10/10* (2015.05); *Y02W 10/30* (2015.05)

(58) Field of Classification Search
CPC ...... D21C 5/005; D21C 5/025; D21H 17/005; D21H 21/24; D21H 21/36; Y02W 30/64; Y02W 10/10; Y02W 10/30; A01N 63/30; A01N 63/20; A01N 63/32; A01N 37/44; C12N 1/16; C12N 1/165; C12N 1/18; C12N 1/185; C12N 2500/74; C12R 2001/645; C12R 2001/72; C12R 2001/85; C12R 2001/86; C12R 2001/865; C12R 2001/87; C02F 3/347; C02F 3/02; C02F 3/28; C02F 11/04; C02F 3/282; C02F 3/342; C02F 2101/32; C02F 2103/007; C02F 2301/106; C02F 2303/02; C02F 2303/10; C02F 2305/04; C02F 3/34; C02F 2303/06; C12P 5/023; Y02E 50/30
See application file for complete search history.

(56) References Cited

U.S. PATENT DOCUMENTS

| | | | |
|---|---|---|---|
| 3,635,797 | A | 1/1972 | Battistoni et al. |
| 4,052,858 | A | 10/1977 | Jeppson |
| 4,541,986 | A | 9/1985 | Schwab et al. |
| 4,666,606 | A | 5/1987 | Heinicke |
| 4,758,353 | A | 7/1988 | Spence et al. |
| 4,804,478 | A | 2/1989 | Tamir |
| 5,071,765 | A | 12/1991 | Wiatr |
| 5,075,008 | A | 12/1991 | Chigusa et al. |
| 5,139,945 | A | 8/1992 | Liu |

(Continued)

FOREIGN PATENT DOCUMENTS

| | | |
|---|---|---|
| CA | 1124459 A | 6/1982 |
| CN | 101557249 A | 10/2009 |

(Continued)

OTHER PUBLICATIONS

Machine Translation of FR 2670798. Published Jun. 26, 1992. (Year: 1992).*

(Continued)

*Primary Examiner* — Renee Claytor
*Assistant Examiner* — Susan E. Fernandez
(74) *Attorney, Agent, or Firm* — UltimatEdge IP Law Group, P.C.; Dean G. Stathakis

(57) ABSTRACT

The present invention provides a process for the treatment of sewage sludge with enzymes, which process comprises treating a sewage sludge resulting from the treatment of municipal or industrial waste water with a composition comprising a fermentation supernatant product from a *Saccharomyces cerevisiae* culture and a non-ionic surfactant, wherein said fermentation supernatant product is free of active enzymes, at conditions suitable for generating said active enzymes from said sewage sludge in situ.

20 Claims, No Drawings

(56) References Cited

U.S. PATENT DOCUMENTS

| | | |
|---|---|---|
| 5,179,003 A | 1/1993 | Wolf et al. |
| 5,227,067 A | 7/1993 | Runyon |
| 5,284,844 A | 2/1994 | Lorenz et al. |
| 5,308,449 A | 5/1994 | Fuentes et al. |
| 5,326,477 A | 7/1994 | Fuqua et al. |
| 5,369,031 A | 11/1994 | Middleditch et al. |
| 5,407,577 A | 4/1995 | Nghiem |
| 5,462,868 A | 10/1995 | Britt et al. |
| 5,500,306 A | 3/1996 | Hsu et al. |
| 5,616,479 A | 4/1997 | Marchal et al. |
| 5,654,192 A | 8/1997 | Ducreux et al. |
| 5,736,209 A | 4/1998 | Andersen et al. |
| 5,820,758 A | 10/1998 | Dale et al. |
| 5,849,566 A | 12/1998 | Dale et al. |
| 5,866,376 A | 2/1999 | Rocha et al. |
| 5,879,913 A | 3/1999 | Marchal et al. |
| 5,879,928 A | 3/1999 | Dale et al. |
| 5,885,590 A | 3/1999 | Hunter et al. |
| 5,885,950 A | 3/1999 | Dale et al. |
| 6,001,218 A | 12/1999 | Hsu et al. |
| 6,699,391 B2 | 3/2004 | Baldridge et al. |
| 6,783,679 B1 | 8/2004 | Rozich |
| 6,841,572 B2 | 1/2005 | Horst et al. |
| 6,884,351 B1 | 4/2005 | Lytal |
| 7,165,561 B2 | 1/2007 | Baldridge et al. |
| 7,476,529 B2 | 1/2009 | Podella et al. |
| 7,645,730 B2 | 1/2010 | Baldridge et al. |
| 7,658,848 B2 | 2/2010 | Baldridge et al. |
| 7,659,237 B2 | 2/2010 | Baldridge et al. |
| 7,759,301 B2 | 7/2010 | Baldridge et al. |
| 7,922,906 B2 | 4/2011 | Baldridge et al. |
| 8,188,028 B2 | 5/2012 | Baldridge et al. |
| 8,389,459 B2 | 3/2013 | Baldridge et al. |
| 8,735,338 B2 | 5/2014 | Baldridge et al. |
| 8,821,646 B1 | 9/2014 | Miller et al. |
| 8,835,152 B2 | 9/2014 | Podella |
| 8,871,682 B2 | 10/2014 | Podella et al. |
| 8,871,698 B2 | 10/2014 | Podella et al. |
| 8,894,861 B2 | 11/2014 | Podella et al. |
| 9,051,535 B2 | 6/2015 | Goldfeld et al. |
| 9,617,178 B2 | 4/2017 | Dale |
| 10,334,856 B2 | 7/2019 | Dale et al. |
| 2002/0187220 A1 | 12/2002 | Luhadiya |
| 2003/0121868 A1 | 7/2003 | Barak |
| 2004/0180411 A1 | 9/2004 | Podella et al. |
| 2005/0164355 A1 | 7/2005 | Vlasenko et al. |
| 2005/0171275 A1 | 8/2005 | De et al. |
| 2005/0266036 A1 | 12/2005 | Awada et al. |
| 2006/0151387 A1 | 7/2006 | Yost et al. |
| 2006/0205042 A1 | 9/2006 | Aehle et al. |
| 2007/0029264 A1 | 2/2007 | Bowe |
| 2007/0224249 A1 | 9/2007 | Kelly et al. |
| 2007/0257127 A1 | 11/2007 | Iverson |
| 2008/0138327 A1 | 6/2008 | Kelly |
| 2008/0293813 A1 | 11/2008 | Agvald et al. |
| 2009/0152196 A1 | 6/2009 | Podella |
| 2009/0186761 A1 | 7/2009 | Arbogast et al. |
| 2010/0078307 A1 | 4/2010 | Dale et al. |
| 2010/0273495 A1 | 10/2010 | Onggosanusi et al. |
| 2011/0052514 A1 | 3/2011 | Juesten et al. |
| 2012/0100236 A1 | 4/2012 | Asolkar et al. |
| 2012/0172219 A1 | 7/2012 | Podella et al. |
| 2013/0104264 A1 | 4/2013 | Schoonneveld-Bergmans et al. |
| 2013/0281328 A1 | 10/2013 | Podella et al. |
| 2013/0344554 A1 | 12/2013 | Bleyer et al. |
| 2014/0056853 A1 | 2/2014 | Marrone et al. |
| 2014/0248373 A1 | 9/2014 | Michalow et al. |
| 2015/0045220 A1 | 2/2015 | Michalow et al. |
| 2015/0072917 A1 | 3/2015 | Baldridge et al. |
| 2015/0141311 A1 | 5/2015 | Podella et al. |
| 2015/0191748 A1 | 7/2015 | Dale |
| 2015/0267151 A1 | 9/2015 | Goldfeld et al. |
| 2016/0100587 A1 | 4/2016 | Bywater-Ekegard et al. |
| 2016/0298056 A1 | 10/2016 | Baldridge et al. |
| 2016/0353746 A1 | 12/2016 | Dale |
| 2016/0362834 A1 | 12/2016 | Dale |
| 2017/0156343 A1 | 6/2017 | Michalow et al. |

FOREIGN PATENT DOCUMENTS

| | | | |
|---|---|---|---|
| CN | 101951686 A | 1/2011 | |
| EP | 375615 A2 | 6/1990 | |
| EP | 1721966 A1 | 11/2006 | |
| FR | 2670798 A1 * | 6/1992 | ............. C12P 19/44 |
| KR | 20100088758 A | 8/2010 | |
| WO | 1992011381 A1 | 7/1992 | |
| WO | 1994012718 A1 | 6/1994 | |
| WO | 1996000811 A1 | 1/1996 | |
| WO | 1997016381 A1 | 5/1997 | |
| WO | 1997028092 A1 | 8/1997 | |
| WO | 1998005212 A1 | 2/1998 | |
| WO | 1998023813 A1 | 6/1998 | |
| WO | 2001079450 A1 | 10/2001 | |
| WO | 2003031536 A1 | 4/2003 | |
| WO | 2003037066 A2 | 5/2003 | |
| WO | 2005019527 A1 | 3/2005 | |
| WO | 2005067531 A2 | 7/2005 | |
| WO | 2005069849 A2 | 8/2005 | |
| WO | 2006119052 A2 | 11/2006 | |
| WO | 2010115021 A2 | 10/2010 | |
| WO | 2010148535 A1 | 12/2010 | |
| WO | 2011016008 A1 | 2/2011 | |
| WO | 2012040908 A1 | 4/2012 | |
| WO | 2013180756 A1 | 12/2013 | |
| WO | 2017035099 A1 | 3/2017 | |
| WO | 2017035100 A1 | 3/2017 | |
| WO | 2017035101 A1 | 3/2017 | |

OTHER PUBLICATIONS

U.S. Appl. No. 14/404,917, filed May 24, 2013, US 2015/0191748, U.S. Pat. No. 9,617,178.
U.S. Appl. No. 15/444,093, filed Feb. 27, 2017, US 2017/0166467.
U.S. Appl. No. 15/243,957, filed Aug. 22, 2016, US 2016/0360758, U.S. Pat. No. 10,334,856.
U.S. Appl. No. 15/243,958, filed Aug. 22, 2016, US 2016/0362834, U.S. Pat. No. 10,557,234.
U.S. Appl. No. 15/243,961, filed Aug. 22, 2016, US 2016/0353746.
U.S. Appl. No. 16/446,583, filed Jun. 19, 2019, US 2019/0307130.
U.S. Appl. No. 16/729,236, filed Dec. 27, 2019.
U.S. Appl. No. 16/729,240, filed Dec. 27, 2019.
Chaichi, et al., "Surfactant Application on Yield and Irrigation Water Use Efficiency in Corn under Limited Irrigation", Crop Sci. 55(1): 386 (2015).
Desai, et al., "Microbial Production of Surfactants and Their Commercial Potential", Microbiol. Mol. Biol. Rev., 1997, 61(1): 47-64.
EPO, Extended Search Report for European Patent Application Serial No. EP13796699.0, p. 12 (dated Jul. 12, 2016).
EPO, Extended Search Report for European Patent Application Serial No. EP16839956.6, p. 12 (dated Jan. 14, 2019).
EPO, Extended Search Report for European Patent Application Serial No. EP16839957.4, p. 11 (dated Apr. 17, 2019).
EPO, Extended Search Report for European Patent Application Serial No. EP16839958.2, p. 12 (dated Sep. 30, 2019).
EPO, Extended Search Report for European Patent Application Serial No. EP19160826.4, p. 5 (dated Apr. 3, 2019).
Frolund, et al., "Enzymatic Activity in the Activated-Sludge Floc Matrix", Appl. Microbiol. Biotechnol., 1995, 43(3): 755-561.
Goel, "Enzyme Activities under Anaerobic and Aerobic Conditions in Activated Sludge Sequencing Batch Reactor", Water Research, 1998, 32(7): 2081-2088.
Ito, et al., "Sophorolipids from Torulopsis bombicola: Possible Relation to Alkane Update", Appl. Environ, Micobiol., 1982, 43(6): 1278-1283.
Kastner, "Formation of Bound Residues during Microbial Degradation of [14C]Anthracene in Soil", Appl. Environ. Microbiol., 1999, 65(5): 1834-1842.

(56) References Cited

OTHER PUBLICATIONS

Sensient Flavors LLC, "Tastone 154, Technical Information", 2010.
Sukumaran, et al., "Microbial Celluloses—Production, Applications, and Challenges", J. Sci. Indus. Res., 2005, 64: 832-844.
WIPO, PCT Form IB373, International Preliminary Report on Patentability for International Patent Application Serial No. PCT/US2013/000140, p. 12 (dated Dec. 2, 2014).
WIPO, PCT Form IB373, International Preliminary Report on Patentability for International Patent Application Serial No. PCT/US2016/048092, p. 6 (dated Mar. 8, 2018).
WIPO, PCT Form IB373, International Preliminary Report on Patentability for International Patent Application Serial No. PCT/US2016/048093, p. 5 (dated Mar. 8, 2018).
WIPO, PCT Form IB373, International Preliminary Report on Patentability for International Patent Application Serial No. PCT/US2016/048094, p. 5 (dated Feb. 27, 2018).
WIPO, PCT Form ISA210, International Search Report for International Patent Application Serial No. PCT/US2013/000140, p. 2 (dated Jul. 22, 2013).
WIPO, PCT Form ISA210, International Search Report for International Patent Application Serial No. PCT/US2016/048092, p. 10 (dated Nov. 15, 2016).
WIPO, PCT Form ISA210, International Search Report for International Patent Application Serial No. PCT/US2016/048093, p. 8 (dated Oct. 24, 2016).
WIPO, PCT Form ISA210, International Search Report for International Patent Application Serial No. PCT/US2016/048094, p. 7 (dated Nov. 4, 2016).
WIPO, PCT Form ISA237, Written Opinion for International Patent Application Serial No. PCT/US2013/000140, p. 11 (dated Jul. 22, 2013).
WIPO, PCT Form ISA237, Written Opinion for International Patent Application Serial No. PCT/US2016/0048093, p. 4 (dated Oct. 24, 2016).
WIPO, PCT Form ISA237, Written Opinion for International Patent Application Serial No. PCT/US2016/048092. pp. 5 (dated Nov. 15, 2016).
WIPO, PCT Form ISA237, Written Opinion for International Patent Application Serial No. PCT/US2016/048094, p. 4 (dated Nov. 4, 2016).
Witek-Krowiak, et al., "Ultrafiltrative Separation of Rhamnolipid from Culture Medium", World J. Microbiol. Biotechnol., 2011, 27: 1961-1964.
Xu, et al., "Biosurfactants for Microbubble Preparation and Application", Int. J. Mol. Sci., 2011, 12: 462-475.
Xu, et al., "Research Review of Wastewater Treatment Technology with Hydrolytic Enzymes", J. Chongqing Univ. Sci. Technol. 12(6), 2010, 156-161.

\* cited by examiner

PROCESS FOR TREATING CONTAMINATED WATER

This application is a continuation is a continuation that claims the benefit of priority and the filing date pursuant to 35 U.S.C. § 120 of U.S. patent application Ser. No. 15/444,093, filed Feb. 27, 2017, a divisional application that claims the benefit of priority and the filing date pursuant to 35 U.S.C. § 121 to U.S. patent application Ser. No. 14/404,917, filed Dec. 1, 2014, now U.S. Pat. No. 9,617,178, a 35 U.S.C. § 371 national phase filing of International Patent Application PCT/US2013/000140, filed May 22, 2013, which claims the benefit of priority and is entitled to the filing date of U.S. Provisional Patent Application 61/689,077, filed May 29, 2012, each of which is hereby incorporated by reference in its entirety.

BACKGROUND OF THE INVENTION

1. Field of the Invention

The invention relates to a process for biologically treating organic materials. In particular, this invention provides a process for treating sewage sludge resulting from the treatment of municipal waste waters and the like to remove volatile solids and other contaminants and generate biogas.

2. Description of the Related Art

Since the passage of the Clean Water Act many industries have been required to institute treatment programs for the waste water they generate before these waters are discharged into public drains and waterways. These programs often include on-site waste water treatment processes, discharge into public treatment works or both.

Waste water is the term used for water which has been changed after household, commercial and industrial use, in particular water which is contaminated and flows and passes into the drainage channels.

Waste water typically contains a wide variety of contaminants which must be removed prior to discharge into public waterways and such contaminants include: organic matter, such as proteins, carbohydrates and lipids; chemicals, such as pesticides, insecticides, heavy metals and fertilizers; and sewage. The waste water is typically assessed in terms of its biochemical oxygen demand (BOD), total suspended solids (TSS) and dissolved oxygen (DO). Another important class of constituents that must be removed from waste water is the volatile organic compounds (VOC) which cause or contribute to the odor of waste water.

A number of processes have been developed which are directed at specific contaminants found in waste water, for example: phenol oxidases and hydrogen peroxide have been used to decolorize pulp and paper mill waste water (U.S. Pat. No. 5,407,577); enzymes from an atypical strain of *Bacillus stearothermophilus* have been used to degrade algal cell walls (U.S. Pat. No. 5,139,945); a combination of bacteria and enzymes have been used to improve the water quality of standing bodies of water (U.S. Pat. No. 5,227,067); cellulases have been used to digest wood/paper compositions (U.S. Pat. No. 5,326,477); *Xanthomonas maltophilia* and *Bacillus thuringiensis* have been used to degrade polar organic solvents (U.S. Pat. No. 5,369,031); yeast has been used to digest carbohydrate-containing waste water (U.S. Pat. No. 5,075,008); a combination of beta.-glucanase, alpha.-amylase and proteases have been used to digest microbial slime (U.S. Pat. No. 5,071,765); and a combination of amylase, lipase and/or proteases have been used to digest colloidal material such as starch, grease, fat and protein (U.S. Pat. No. 5,882,059). However, each of these compositions are directed at only a specific contaminant and they do not address the variety of contaminants which are usually found in waste water and other polluted water. A composition described in U.S. Pat. No. 3,635,797 used a yeast fermentation composition to deodorize sewage ponds and degrade organic waste. However, this composition has been found to be unstable and yielded variable results from one batch to another.

The above processes are generally carried out under aerobic conditions, that is, the treating process requires the presence of oxygen, usually from air.

The present inventors have invented a liquid composition comprising fermentation supernatant from a yeast such as a *Saccharomyces cerevisiae* culture and a non-ionic surfactant, preferably selected from the group consisting of ethoxylated alkylphenols and/or long chain aliphatic alcohols. This liquid composition in combination with the active enzymes, resulting from the fermentation of *Saccharomyces cerevisiae*, has been used under aerobic conditions, as well as anaerobic conditions to treat, among other waste waters, municipal sewage. (See U.S. Pat. Nos. 5,820,758; 5,849,566; 5,879,928; 5,885,590 and published U.S. patent application Ser. No. 12/586,126.) It has now been surprisingly found that a product comprising the combination of a fermentation supernatant from a *Saccharomyces cerevisiae* culture, which is free of active enzymes and a non-ionic surfactant is effective to treat sewage sludge, e.g. a sewage sludge resulting from the treatment of municipal or industrial waste water. This discovery is discussed in more detail below.

The biological treatment of liquids contaminated with organic materials or the purification of waste water to remove organic contaminants, which contaminants are contained in the liquids in a dissolved, colloidal or finely dispersed form, by microbial activity, e.g. by anaerobic degradation, generates a combustible gas, known as biogas.

Generally, waste water is biologically purified in waste treatment plants using the same or similar procedures which occur when the waste water biologically cleans itself in running waters, i.e. under aerobic conditions, albeit, in a technically more intensive manner. In nature, the anaerobic process of biological purification likewise occurs, e.g. at the bottom of flat, still waters.

For the purposes of describing the present invention, it is understood that "treating" means the conversion of organic materials, i.e. contaminants, by means of micro-organisms, e.g. bacteria, in the presence or absence of oxygen. During the process of anaerobic degradation of organic materials, biogas is produced, i.e. a gas mixture which consists of methane, mainly, and carbon dioxide and traces of other ingredients. The process of the invention may also be carried out under aerobic conditions to provide fermentation products from cellulosic feeds, etc.

Methods for biologically treating liquids, containing high amounts of organic materials as contaminants, under anaerobic conditions are known for treating waste waters from the foodstuff industry, agriculture, mineral oil industry as well as from pulp making. In other words, it is possible to treat many 'liquids but, in general, such known biological methods are incapable of providing a full purification or complete conversion of such organic contaminants.

It is one object of this invention to treat an organic waste material, in a bacterial process, by digesting said waste at an elevated temperature to produce biogas, which biogas can be used in generators for electricity production and/or in boilers for heating purposes.

It is another object of the invention to treat sewage sludge in a bacterial process by fermenting said sludge at an elevated temperature to produce a biogas, which can then be used in generators for electricity production and/or in boilers for heating purposes and, in particular said biogas may be used to provide the heat to treat said sewage sludge.

It is another object of the invention to treat sewage sludge in a bacterial process that is carried out by fermenting said sludge at an elevated temperature to reduce the volatile organic solids (VOS).

It is another object of the invention to treat sewage sludge in a bacterial process that is carried out by fermenting said sludge at an elevated temperature to reduce the weight and/or volume of the treated, solid sludge product leaving the process.

Other objects of this invention will become apparent from a reading of the present specification.

SUMMARY OF THE INVENTION

The present invention provides a process for the treatment of organic materials, i.e. organic waste materials, which process comprises the use of a bio-catalytic composition comprising (a) a fermentation supernatant of a yeast formulation which comprises micronutrients, including bio-available minerals and vitamins. The supernatant is pasteurized and denatured and therefore contains no active enzymes or bacteria cultures. The supernatant is blended with (b) one or more nonionic surfactants. The bio-catalytic composition of this invention, when added to a waste water stream containing organic materials, is capable of increasing i) the enzymatic activity of bacterial cultures present in the waste water by increasing the dissolved oxygen needed for respiration and reproduction of said bacteria; and ii) the catalytic action of said bacteria in breaking bonds present in said organic materials to release the organic material as a more digestible form for consumption by said bacteria. Said bio-catalytic composition forms a functionalized surfactant in the form of highly structured, ultra-fine, microbubbles in said waste water, which microbubbles provide a readily available reserve of oxygen in the waste water by encapsulating oxygen therein and increasing the transfer of oxygen across the membrane barrier of the microbubble and the cellular structure of the organic material consumed by the bacteria.

In the process of this invention, the organic waste is preferably treated with a composition comprising fermentation supernatant from a yeast culture, e.g. a *Saccharomyces cerevisiae* culture; and a non-ionic surfactant.

In one preferred embodiment of the process of this invention, the organic waste comprises sewage sludge, which is treated in a process that comprises, either, thermophilic digestion, in which sludge is fermented in tanks at a temperature of about 55-60° C., or mesophilic digestion, wherein said process is carried out at a temperature of about 35-40° C. The methane in biogas can be burned to produce both heat and electricity, usually with a reciprocating engine or turbine, or fed to fuel cells often in a cogeneration arrangement where the electricity and waste heat generated are used to warm the digesters or to heat buildings. Excess electricity can be sold to suppliers or put into the local grid. Electricity produced by anaerobic digesters is considered to be renewable energy and may attract subsidies. Biogas does not contribute to increasing atmospheric carbon dioxide concentrations because the gas is not released directly into the atmosphere and the carbon dioxide comes from an organic source with a short carbon cycle.

In this preferred embodiment of the process of the invention, a combustible biogas is produced, which comprises methane, and can be used in generators for electricity production and/or in boilers for heating purposes.

In another preferred embodiment of the process of this invention said nonionic surfactant is selected from the group consisting of Alkyl Polysaccharides, Alkylamine Ethoxylates, Amine Oxides, Block Copolymers, Castor Oil Ethoxylates, Ceto-Oleyl Alcohol Ethoxylates, Ceto-Stearyl Alcohol Ethoxylates, Decyl Alcohol Ethoxylates, ethoxylated dodecyldecanol and ethoxylated tridecyldecanol, and other $C_{12}$-$C_{14}$ secondary aliphatic alcohol ethoxylates, or the nonionic surfactant may be a nonyl or octyl phenol adduct comprising from 20 to 40 moles ethylene oxide, e. g. about 30 moles ethylene oxide.

DETAILED DESCRIPTION OF THE INVENTION

Oxidative biological and chemical processes in aqueous environments are limited by the low solubility of oxygen in water. This physical limitation is defined by Henry's Law. It states that when the temperature is kept constant, the amount of a gas that dissolves into a liquid is proportional to the pressure exerted by the gas on the liquid.

The solubility of oxygen in pure water is only about 10 parts per million (ppm) at ambient temperatures and at one atmosphere pressure. The composition of the present invention has been observed to increase oxygen in water above levels, which would be anticipated by Henry's Law.

For most aerobic bioprocesses, whether a wastewater treatment system or a biotechnology fermentation, dissolved oxygen is quickly consumed so that replenishing it becomes the factor which limits the rate of the process. Therefore, the most critical component of a bioprocess design is the means for the mass transfer of oxygen into the liquid phase of the process. For an actively respiring culture of bacteria at a cell density of about 10-9 cells/ml, oxygen in the liquid medium must be replaced about 12 times per minute to keep up with the oxygen demand of the bacteria.

Water is typically aerated by increasing the contact surfaces between the gaseous and liquid phases. This can be done either by introducing a source of oxygen into a bulk liquid phase or by flowing dispersed water through a bulk gaseous (air) phases. Regardless of whether the gaseous or liquid phases dominate the oxygenation process, the mass transfer of oxygen, or other gas, is accomplished by introducing gas bubbles into the liquid phase. The efficiency of gas-liquid mass transfer depends to a large extent on the characteristics of the bubbles. Bubble behavior strongly affects the following mass-transfer parameters: Transfer of oxygen from the interior of the bubble to the gas-liquid interface; Movement of oxygen across the gas-liquid interface; and Diffusion of oxygen through the relatively stagnant liquid film surrounding the bubble.

It is of fundamental importance in the study of bubbles to understand the exchange of gases across the interface between the free state within the bubble and the dissolved state outside the bubble. It is generally agreed that the most important property of air bubbles in a bioprocess is their size. For a given volume of gas, more interfacial area (a) between the gas phase and liquid phase is provided if the gas is dispersed into many small bubbles rather than a few large ones. Small bubbles, 1-3 mm, have been shown to have the following beneficial properties not shared by larger bubbles:

Small gas bubbles rise more slowly than large bubbles, allowing more time for a gas to dissolve in the aqueous phase. This property is referred to as gas hold-up, concentrations of oxygen in water can be more than doubled beyond Henry's Law solubility limits. For example, after a saturation limit of 10 ppm oxygen is attained; at least another 10 ppm oxygen within small bubbles would be available to replenish the oxygen.

Once a bubble has been formed, the major barrier for oxygen transfer to the liquid phase is the liquid film surrounding the bubble. Biochemical engineering studies have concluded that transport through this film becomes the rate-limiting step in the complete process, and controls the overall mass-transfer rate. However, as bubbles become smaller, this liquid film decreases so that the transfer of gas into the bulk liquid phase is no longer impeded.

Surfactants in water can lead to the formation of very small bubbles, less than 1 mm in diameter. These small bubbles, referred to as microbubbles, are the result of the reduced surface tension at the interface between the gas/liquid interface caused by surfactants.

As large concentrations of gas are introduced into a solution such as by a chemical reaction or other mechanism, the liquid phase can become supersaturated if nucleation centers for the formation of bubbles are absent. At this point microbubbles can then form spontaneously, nucleating large bubble formation, and sweeping dissolved gases from the solution until super saturation again occurred. In the presence of surfactants, it is likely that a larger portion of gas would remain in the solution as stable bubbles.

Microbubbles exposed to a dispersion of gas in a liquid show colloidal properties and are referred to as colloidal gas aphrons (CGA). CGA differ from ordinary gas bubbles in that they contain a distinctive shell layer consisting of a low concentration of a surfactant.

The composition of the present invention exhibits desirable properties associated with surfactant microbubbles. However, the microbubbles formed with the composition of the present invention appear to increase the mass transfer of oxygen in liquids. Without being bound by scientific theory, there are several possible explanations for this difference:

The earlier described surfactant microbubbles involved the use of pure synthetic surfactants that were either anionic or cationic. The surfactants formulated into the composition of the present invention are nonionic and are blended with biosurfactants which significantly alter the properties of bubble behavior.

The composition of the present invention requires a much lower concentration of surfactants for microbubble formation. It has been suggested that surfactant concentrations must approach the critical micelles concentration (CMS) of a surfactant system. In the composition of the present invention, microbubbles are formed below estimated CMCs for the surfactants used. This suggests that the composition of the present invention microbubbles are the result of aggregates of surfactant molecules with a loose molecular packing more favorable to gas mass transfer characteristics. A surface consisting of fewer molecules would be more gas permeable than a well-organized micelle containing gas.

In addition to surfactants, the composition of the present invention contains biologically derived catalysts. Both of these components tend to be amphiphilic, that is they have pronounced hydrophobic and hydrophilic properties. Amphiphilic molecules tend to cluster in water to form and allow molecular weight aggregates which (as surfactant concentrations increase) result in micelle formation at concentrations ranging from $10^{-2}$ to $10^{14}$ M. Aggregates of these amphiphilic molecules are the nuclei for microbubble formation.

The composition of the present invention appears to increase oxygen levels in fluids. Without being bound by scientific theory, it is believed this effect can be explained by either or both of two mechanisms: Increased mass transfer of gases resulting from the interactions of non-ionic surfactants and other components of the composition of the present invention; and Delayed release of gases from microbubbles so that oxygen can be dispersed throughout a liquid rather than just at the point of introduction.

With either mechanism, it is likely that the tendency of composition of the present invention organizes into clusters, aggregates, or gas-filled bubbles provides a platform for reactions to occur by increasing localized concentrations of reactants, lowering the transition of energy required for a catalytic reaction to occur, or some other mechanism which has not yet been described. It has been established that the non-ionic surfactants used in the composition of the present invention are compatible with and enhance enzymatic reactions. The composition of the present invention has catalytic activities that is more like the catalytic activities of functionalized surfactants than conventional enzyme systems.

The composition of the present invention comprises a yeast fermentation supernatant and a non-ionic surfactant, in the absence of active enzymes and anionic or cationic surfactants. Non-ionic surfactants suitable for use in the present invention include, but are not limited to, polyether non-ionic surfactants comprising fatty alcohols, alkyl phenols, fatty acids and fatty amines which have been ethoxylated; polyhydroxyl non-ionic (polyols) typically comprising sucrose esters, sorbital esters, alkyl glucosides and polyglycerol esters which may or may not be ethoxylated. In one embodiment of the present invention a surfactant of the general formulae:

and in particular an ethoxylated octyl phenol which is sold under the tradename IGEPAL CA-630, is used. The non-ionic surfactant acts synergistically to enhance the action of the yeast fermentation supernatant.

These micro-bubbles and their highly reactive oxygen transfer capabilities thereby act as a broad-spectrum facilitator of vastly accelerated biological, and chemical reactions, in situ, within water, wastewater, and organic solids, far exceeding in speed and magnitude bacterial enzymatic types reactions available through either active enzymes, cultivated bacterial cultures, or existing surfactant products.

The new 'functionalized surfactant' composition produces micro-bubbles that are much smaller than the air bubbles produced mechanically by aeration systems. The most critical element to biologically degrading organic pollutants in wastewater systems, or purifying water, is the supply of oxygen that resides in the water column that supports the biological processes, or oxidation reactions of purification chemicals.

Mechanism of action is two-fold: One, formation of micro-bubbles of the 'functionalized surfactant' with its highly reactive bubble shells, allows a reservoir of dissolved oxygen to be built up in the water column far exceeding the normal level according to Henry's Law of dissolved oxygen available through mechanical aeration systems. Two, the highly reactive membrane bubble shells of the 'functionalized surfactant' micro-bubbles allow for a very enhanced oxygen transfer capability far exceeding micro-bubbles formed by the composition's blended surfactants. Thus, the micro-bubbles resulting from the use of the compositions of this invention provides a foundation for improving biological and chemical reactions:

Availability of dissolved oxygen in water is critical limiting factor in the respiration required by microorganisms in consumption of organic pollutants through biological oxidation-reductions. Speed of biological reductions is a critical part of the design, hydraulic loading, quality of discharges, and operational efficiency of any wastewater treatment system.

The twin aspects of the invention's micro-bubbles; increased dissolved oxygen reservoirs, and enhanced oxygen transfer across membrane barriers, work synergistically in allowing a substantial positive expansion of the availability of dissolved oxygen to the microorganisms in their consumption of organic pollutants. The result is a much greater efficiency of wastewater biological treatment processes, or the oxidative capabilities of various chemicals oxidation agents, such as chlorine, sodium hypochlorite, ferric chloride, peroxide, etc.

Oxidative chemicals are used broadly to sanitize polluted water of organic contaminates to prevent biological growth from such organics within the water. Enhancing oxygen transfer and dissolved oxygen within the water column will allow a much greater efficiency of the chemical processes required in sanitizing the water, resulting in reduced consumption of the oxidizing chemical in the process.

In addition to enhancing the biological and chemical processes used in water purification and wastewater treatment, the same mechanisms of action have shown the capability to increase the speed of biological reductions in composting of organic waste solids and the rate of remediation of petroleum hydrocarbon pollutants.

The acceleration of composting and remediation rates is due to the enhanced oxygen transfer across cellular membranes of the organic solids. Efficacy of the new composition is enhanced when combined with an immediate neutralization of volatile organic compounds (VOCs), often characterized by noxious odor profiles.

A corollary attribute of enhanced oxygen transfer is the efficient solubilization of insoluble organic wastes components, such as fats, oils, and greases. The ability of the compositions of the present invention to cleave ester bonds of fats, oils, and greases lies in the ability to allow a gas transfer across the membrane barriers of the molecular structure which thereby effects a breaking of the ester bonds linking glycerol and fatty acids. This is a form of hydrolysis that is pH neutral, rather than due to very high pH, or very low pH agents, or lipase enzymes. Lipases are the specific group of enzymes generally attributed to the cleaving of the ester bonds, however, the compositions of the present invention initiates the same cleaving mechanism of breaking the ester bonds, by way of the oxygen transfer mechanism, i.e.; beta-oxidation.

This ability to effect a solubilization of these insoluble organic molecules, thereby releasing the organic components into a more readily digestible form for their consumption by microorganisms, works again synergistically with the benefits bestowed by increased oxygen availability, which aids the biological respiration reduction required in aerobic biological processes.

In cleaning of surfaces of fats, oils, and greases, the breaking of the ester bonds renders a much improved surface cleaning due to a substantial reduction in the residual waste components left on the surface and drain lines receiving the waste stream.

The compositions of the present invention have been found to be useful in the following processes:

Water Purification:

When used in swimming pools chlorine consumption rates are reduced up to 70% depending upon usage, mineralization scaling is substantially reduced, filters are cleaned, and backwashing of settled oxidized residues substantially reduced.

Wastewater Treatment:

When used in wastewater treatment systems aeration energy usage can be reduced up to 50%, higher organic loadings can be processed under hydraulic volumes previously unable to provide adequate dissolved oxygen levels for biological reduction discharge requirements. Sludge/Solids can be reduced up to 35% due to greater solubility of the organic molecular structure of the waste stream.

Odor Control in Sewer Lines & Pump Stations:

When used in sewer lines and pump stations $H_2S$ gas levels can be substantially reduced through a new preventative model where the biological film growth (slime layers) is dissolved away thereby eliminating a critical source of dissolved sulfides which evolve as $H_2S$ gas. Formation of ultra-fine micro-bubbles also provides a higher level of dissolved oxygen in the bulk sewage water thereby preventing $H_2S$ gas evolution as $H_2S$ will not tend to evolve from dissolved sulfides in water with dissolved oxygen levels over 1.1 ppm.

Odor Control:

When used on a high dilution in water spraying, the compositions of the present invention provide an immediate odor neutralization of odorous waste materials, surfaces, and septic water bodies. Additionally, when misted an extremely high dilutions (1500×1) or greater, it will neutralize noxious gases within the air column.

Petroleum Hydrocarbon Remediation:

When used in a petroleum hydrocarbon remediation protocol, Total Petroleum Hydrocarbon (TPH) reductions are accelerated substantially over baseline rates of remediation, due to greatly enhanced solubility of the molecular structure of the hydrocarbons. Cleaning of surfaces is also greatly enhanced due to the solubility enhancement capabilities of the new composition.

Ecological Restoration of Rivers and Water Bodies:

When applied through a spraying onto the surface of the water on a diluted basis there is created an upper surface zone of higher dissolved oxygen, which acts as to oxidize anaerobic gases evolving from the sludge on the bottom of the river or water body. Additionally, this upper zone of dissolved oxygen containing the composition's micro-bubbles acts as a cleaning mechanism on the biological film growth (slime layers) that forms along the sides of the riverbank.

Composting:

When used in composting piles, the composition provides instantaneous odor elimination when sprayed a high dilutions upon the pile forming an aerobic upper zone in the organic materials being composted. Additionally, the rate of composting (a biological consumption) is accelerated and the production of VOC gases (greenhouse) is reduced.

FOG Cleaning:

When used in the cleaning of wastes containing high levels of fats, oils, and greases, such as meat rooms, slaughter houses, food processors, the improved solubility capability of the composition breaks down the waste lipid molecular structure so that these wastes do not reform structurally downstream in drains, and there is a deep subsurface cleaning of surfaces.

Cleaning of Animal Wastes:

When used in the cleaning of animal containment operations, such as stables, animal feeding operations, and dairies, the composition acts immediately upon urine (ammonia) and wastes rendering them odorless, preventing the stress on animals from the VOC compounds. Additionally, the animal wastes begin undergoing an immediate breakdown due to the catalytic effect of the composition upon the molecular structure of the waste stream.

Aquaculture:

When used in aquaculture operations the composition allows a rise in dissolved oxygen levels in excess of the levels obtained through mechanical aeration systems deployed. Ammonia, a highly toxic byproduct of fish wastes is more susceptible to oxidation neutralization, and the molecular structure of the fish wastes are broken down into constituents for less accumulation in the water column.

Pulp & Paper:

When used in the manufacture of paper, a substitution of biocide type sanitizing chemical agents is made possible in the pulping tanks, which are traditionally used to prevent biological film growth and spotting in the paper manufacture. Bacterial and pathogen colony counts are reduced, biological film growth eliminated, and spotting is eliminated. Additionally, the build up of starches on the rollers is substantially reduced as the molecular structure of the starches is solubilizes by the composition.

Anaerobic Digestion:

When used in anaerobic digestion systems, this composition solubilizes the waste stream molecular structure, especially the lipid components which are the highest bio-methane waste components, rendering them more easily available for conversion in methangenesis. This is a pH neutral form of hydrolysis. Additionally, the composition's high concentration of bio-available minerals and vitamins provide critical availability of nutrients essential for certain metabolic reactions, or biological consumption of the waste stream.

Soil Conditioning:

When used in watering of plants at very high dilutions, the composition provides a increased solubility of organic components within the soil, enhances the uptake potential of micro-nutrients by the plant's roots, increases permeability of the soil to water, dissolves anaerobic slime growth, and promotes the aerobic conditions within the soil.

The non-ionic surfactants suitable for use in the present invention include, but are not limited to, polyether non-ionic surfactants comprising fatty alcohols, alkyl phenols, fatty acids and fatty amines which have been ethoxylated; polyhydroxyl non-ionic (polyols) typically comprising sucrose esters, sorbital esters, alkyl glucosides and polyglycerol esters which may or may not be ethoxylated. In one embodiment of the present invention the nonionic surfactant is represented by one of the general formulae, below:

$H(OCH_2CH_2)_xOC_6H_4RH(OCH_2CH_2)_xOR^1H$
$(OCH_2CH_2)_xOC(O)R^1$ wherein x represents the number of moles of ethylene oxide added to an alkyl phenol and/or a fatty alcohol or a fatty acid, R represents a long chain alkyl group, e. g. a $C_7$-$C_{10}$ normal-alkyl group and, $R_1$ represents a long chain aliphatic group, e.g. a $C_{12}$-$C_{20}$ aliphatic group in particular, the nonionic surfactant is an ethoxylated octyl phenol or a dodecylalcohol or tridecylalcohol ethoxylate. The non-ionic surfactant acts synergistically to enhance the action of the yeast fermentation supernatant.

The fermentation supernatant product that is utilized in the process of the present invention may be prepared in a manner similar to that described in U.S. Pat. No. 3,635,797 to Battistoni et al., which is hereby incorporated by reference in its entirety. Briefly, yeast, e.g. *Saccharomyces cerevisiae*, is cultured in a medium comprising: a sugar source, such as sucrose from molasses, raw sugar, soybeans or mixtures thereof. A sugar concentration of about 10 to about 30%, by weight; malt such as diastatic malt at a concentration of about 7 to about 12%, by weight; a salt, such as a magnesium salt, and, in particular, magnesium sulfate, at a concentration of about 1 to about 3%, by weight, and yeast are added to the medium to obtain a final concentration of about 1 to about 5%, by weight, of yeast in the final culture mixture. The mixture is incubated at about from 26 degrees to about 42 degrees C. until the fermentation is completed, i.e. until effervescence of the mixture has ceased, usually about 2 to about 5 days depending on the fermentation temperature. At the end of the fermentation the yeast fermentation composition is centrifuged to remove the "sludge" formed during the fermentation. The supernatant (about 98.59%, by weight) may be mixed with preservative or stabilizing system, such as sodium benzoate (about 1%, by weight), imidazolidinyl urea (about 0.01%, by weight), diazolidinyl urea (about 0.15%, by weight), calcium chloride (about 0.25%, by weight) to form a fermentation intermediate. The pH is adjusted to from about 3.7 to about 4.2 with phosphoric acid. The composition of the fermentation intermediate is disclosed in Table I. (Note that the yeast supernatant is treated to eliminate any bacteria and/or active enzyme prior to use in the process of the invention.

TABLE I

| Fermentation Intermediate | |
|---|---|
| Component | %, by weight |
| Fermentation supernatant | 98.59 |
| Na Benzoate | 1 |
| Imidazolidinyl urea | 0.01 |
| Diazolidinyl urea | 0.15 |
| Calcium chloride | 0.25 |

Adjust pH to about 3.7 to about 4.2 with Phosphoric acid

The fermentation intermediate may be prepared by filling a jacketed mixing kettle with the desired quantity of the fermentation supernatant. With moderate agitation the pH is adjusted to from about 3.7 to about 4.2 with phosphoric acid. With continuous agitation, sodium benzoate, imidazolidinyl urea, diazolidinyl urea and calcium chloride are added. The temperature of the mixture is then slowly raised to about 40 degrees C. and the mixture is agitated continuously. The temperature is maintained at about 40 degrees C. for about one hour to ensure that all the components of the mixture are dissolved. The mixture is then cooled to from about 20 degrees to about 25 degrees C.

The fermentation intermediate is then spray dried by methods known in the art to provide a fermentation supernatant product as a dry powder from the *Saccharomyces cerevisiae* culture. Importantly, said dry powder, unlike the liquid fermentation supernatant product prepared by the method disclosed in U.S. Pat. No. 3,635,797 is free of bacteria and the active enzymes found in the liquid product of U.S. Pat. No. 3,635,797.

The fermentation intermediate (the liquid fermentation supernatant product) may be formulated into the composition of the present invention (final composition) by mixing the spray dried fermentation intermediate (about 20.24%, by weight, of the final composition) with, preservatives such as sodium benzoate, imidazolidinyl urea, diazolidinyl urea, imidazolidinyl urea, diazolidinyl urea and mixtures thereof (about 0.16%, by weight, of the final composition), a non-ionic surfactant such as ethoxylated octyl phenol or a dodecyl or tridecylalcohol ethoxylate (about 9%, by weight, of the final composition) and the composition is brought to 100% by the addition of water. In a preferred embodiment of the present invention the composition comprises about 20.24%, by weight, fermentation intermediate, about 0.1%, by weight, sodium benzoate, about 0.01%, by weight, imidazolidinyl urea, about 0.15%, by weight, diazolidinyl urea, about 9%, by weight, ethoxylated octyl phenol or tridecyl-alcohol ethoxylate (See Table II).

TABLE II

Final Composition

| Component | %, by weight |
|---|---|
| Sodium benzoate | 0.1 |
| Imidazolidinyl urea | 0.01 |
| Diazolidinyl urea | 0.15 |
| Ethoxylated octyl phenol or tridecyl alcohol | 9.00 |
| Fermentation Intermediate | 20.24 |

The method for preparing the final composition is as follows: A mixing kettle is charged with the desired volume of water at about 20 degrees to about 25 degrees C. Sodium benzoate, imidazolidinyl urea and diazolidinyl urea are added while the solution is agitated. The mixture is agitated until the solids are dispersed. Ethoxylated octyl phenol or dodecyl or tridecyl alcohol is then added and the agitation is continued. The fermentation intermediate is then added with gentle agitation. The pH is adjusted to about 3.5 to about 4.0 with phosphoric acid.

After mixing and pH adjustment, the final concentration of components in the final composition is summarized in Table III.

TABLE III

Final Composition

| Component | %, by weight |
|---|---|
| Na benzoate | 0.3 |
| Imidazolidinyl urea | 0.01 |
| Diazolidinyl urea | 0.15 |
| Ethoxylated octyl phenol or dodecyl or tridecyl alcohol | 9.0 |
| Calcium chloride | 0.05 |
| Fermentation supernatant | 20 (clarified) |

Adjust pH to about 3.5 to 4.0 with phosphoric acid

The final composition is diluted for use in a zone for treating organic materials in waste water as described below.

Alternatively, a yeast powder is available from commercial sources and said yeast powder may be combined with a nonionic surfactant to provide a composition suitable for practicing the process of this invention. For example, TASTONE 154 (TT154-50) may be formulated with the nonionic surfactant to provide a composition similar to the composition of Table III.

The method for preparing this composition is as follows: A mixing kettle is charged with the desired volume of water at about 20 degrees to about 25 degrees C. Tastone 154 is added while the solution is agitated. The mixture is agitated until the blend is uniform. In sequential steps Tergitol 15-S-7, Tergitol 15-S-5, Dowfax 2A1, Triton H66 and Integra 44 is added with the resulting blend agitated, after each addition, until uniform. The pH is then adjusted to 6+/−0.5 with Phosphoric acid. (Tergitol 15-S-7 and Tergitol 15-S-5 are nonionic surfactants. Dowfax 2A1 and Triton H66 are anionic surfactants. Integra 44 is a biocide.)

After mixing and pH adjustment, the final concentration of components in the final composition is summarized in Table IV.

TABLE IV

Final Composition

| Component | %, by weight |
|---|---|
| Water | 87.238 |
| Tastone 154 | 0.762 |
| Tergitol 15-S-7 | 3.750 |
| Tergitol 15-S-5 | 3.750 |
| Dowfax 2A1 | 1.500 |
| TritonH66 | 2.500 |
| Integra 44 | 0.500 |

Adjust pH to about 6.0 +/− 0.5 with phosphoric acid

For use in treating waste water the final composition, i.e. the composition of TABLE III or IV, is diluted to as high as parts per million. For other uses it may desirable to dilute the final composition only as little as 1 in 10. Those skilled in the art are aware that dilutions of such compositions can be used and that over-dilution for a particular purpose can result in a decreased rate of digestion and that under-dilution for a particular purpose increases cost without increasing the rate of degradation. Ideally, the final composition is diluted to optimize the rate of degradation of a particular waste and to minimize costs.

In use, the composition of the present invention degrades pollutants, by enhancing the activity of bacteria commonly found in waste water treatment plants and, unexpectedly, increases the amount of biogas generated, while decreasing the volatile odorous compounds (VOC) and the volume and weight of the effluent from the treatment zone.

In an aerobic process, wherein the above surfactant and yeast fermentation supernatant composition is utilized to degrade pollutants in the presence of bacteria, DO is decreased as the bacteria metabolize the available oxygen. The nonionic surfactant and yeast fermentation supernatant product act synergistically to enhance the rate of degradation and increase DO. In such aerobic process, the surfactant, alone, or the yeast fermentation supernatant, alone, does not result in the enhanced activity observed when they are combined.

It has been surprisingly found that the compositions of the present invention, even though lacking any active enzymes or bacteria, increase dissolved oxygen levels and oxygen transfer. The compositions of the present invention provide increased dissolved oxygen levels in water bodies, over and above the levels obtained through mechanical means obtained with aerators and air diffusion systems, thus reducing the organic pollutants in said water body.

Moreover, as discussed below, the highly concentrated bio-nutrient concentration of the compositions of the present invention provides stimulation of the microbiological organisms present in said water body.

The combination of the nonionic surfactant and the bio-nutrients in the compositions of the present invention results in a synergistic reduction in the rate of removal of organic contaminants from the water body which is treated with the composition of the present invention.

Thus, the compositions of the present invention are useful in treating contaminated water bodies and closed loop water systems, removing odors, cleaning fats, oils and greases, including petroleum hydrocarbons and breaking down biologically produced structural bio-films.

The mechanisms of action of the compositions of the present invention are directed at two synergistic and complimentary aspects of functionality; accelerated bio-catalysis of the molecular structures of organic wastes, particularly the more refractory lipids and the enhanced oxygen transfer into water.

These twin mechanisms work together in overcoming the limiting factors encountered in all waste water and water treatment applications where oxygen, through aeration, is utilized as the energy required by biological processes to reduce organic pollutants. These twin mechanisms are also relevant to effectively providing an alternative model to biological fouling and biofilm growth in closed loop water heat transfer systems, pulp and paper processing, sewage collection systems, drainage lines, and any water treatment system that utilizes a biocide to subdue the formation of biological fouling and contamination.

In an anaerobic process similar advantages are obtained, by treating the organic waste material with the combination of the above-described surfactant and yeast fermentation supernatant composition. Moreover, like the aerobic process, the enhanced degradation observed in use of the final composition, in an anaerobic process is proportional to the time that the final composition is in contact with the waste water to be treated. Therefore, it is desirable that the final composition is added to the waste water at the earliest opportunity. Preferably, the final composition is added upstream of the anaerobic or aerobic zone of the waste water treatment plant. The final composition may be added to the waste water by continuously pumping the final composition into the waste water or it may be added in batches as desired to reach the desired dilution of the final composition in the anaerobic or the aerobic zone.

While not wishing to be bound by theory, is believed that the waste water stream to be treated benefits from the bio-nutrients present in the yeast fermentation supernatant by feeding the bacteria already present in the waste water to thereby increase the concentration of said bacteria and/or otherwise enhancing the activity of said bacteria by increasing the amount of enzyme generated by the already present bacteria. Thus, the yeast fermentation supernatant does not require the presence of active enzyme to carry out the process of the present invention but rather the active enzyme of interest is generated in-situ.

The fermentation supernatant may comprise the following bio-nutrients in the following amounts:

| Vitamins mg/100 g | Preferred | Range |
|---|---|---|
| Biotin | 0.1 | 0.01-1 |
| Folic Acid | 5.6 | 1.0-10.0 |
| Niacin | 54.1 | 10.0-90.0 |
| Insotil | 130 | 10.0-250 |
| Pantothenic Acid | 7.3 | 1.0-10.0 |
| Pyrodoxine HCl | 5.6 | 1.0-10.0 |
| Riboflavin | 12 | 1.0-20.0 |
| Thiamine | 8.3 | 1.0-20.0 |

| Minerals mg/100 g | |
|---|---|
| Ca | 141 |
| Cr | 0.4 |
| Cu | 0.2 |
| Fe | 8.5 |
| Mg | 208 |
| P | 1770 |
| K | 3790 |
| Na | 2660 |
| Zn | 1380 |

| Amino Acids mg/100 g | |
|---|---|
| Alanine | 3980 |
| Arginine | 2640 |
| Aspartic acid | 5800 |
| Cystine | 568 |
| Glutamic acid | 7520 |
| Glycine | 2800 |
| Lysine | 4570 |
| Methionine | 964 |
| Phenylalanine | 2450 |
| Proline | 2180 |
| Serine | 2840 |
| Threonine | 2730 |

Thus, the compositions used in the process of this invention may comprise an enzyme-free fermentation supernatant product from a yeast culture, e.g. a *Saccharomyces cerevisiae* culture, in combination with a nonionic surfactant, wherein said supernatant product comprises sufficient types and amounts of bio-nutrients to generate the bacteria necessary to treat the waste water stream in situ. For example, said composition may comprise:

TABLE V

| Ingredient | Wt. % |
|---|---|
| Nonionic surfactant, e.g. ethoxylated octyl phenol or dodecyl or tridecyl alcohol | 1.0-15.0 |
| Fermentation supernatant product from a yeast culture, e.g. a *Saccharomyces cerevisiae* culture | 5.0-35.0 |
| Water to 100 wt. % | |

Preferably, said composition may comprise:

TABLE VI

| Component | Wt. % |
|---|---|
| Na benzoate | 0.3 |
| Imidazolidinyl urea | 0.01 |
| Diazolidinyl urea | 0.15 |
| Ethoxylated octyl phenol or dodecyl or tridecyl alcohol | 9.0 |
| Calcium chloride | 0.05 |
| Fermentation supernatant from Table III | 20 | or

TABLE VII

| Component | %, by weight |
|---|---|
| Yeast powder available as Tastone 154 | 0.5-1.5 |
| Ethoxylated dodecyl or tridecyl alcohol | 5-10 |
| Anionic surfactant | 2-6 |
| Biocide | 0.1-1.0 |
| Water to 100 wt. % | |

The above fermentation supernatant product, i.e. the spray dried powder from the *Saccharomyces cerevisiae* culture of TABLE III or Tastone 154 may comprise vitamins, minerals and amino acids as follows:

| Vitamins | Minerals | Amino Acids |
|---|---|---|
| Biotin | Ca | Alanine |
| Folic Acid | Cr | Arginine |
| Niacin | Cu | Aspartic acid |
| Insotil | Fe | Cystine |
| Pantothenic Acid | Mg | Glutamic acid |
| Pyrodoxine HCl | P | Glycine |
| Riboflavin | K | Lysine |
| Thiamine | Na | Methionine |
| | Zn | Phenylalanine |
| | | Proline |
| | | Serine |
| | | Threonine |

The invention is further illustrated by the following examples which are illustrative of a specific mode of practicing the invention and are not intended as limiting the scope of the claims.

Example 1

The process of the present invention may be exemplified by the treatment of the discharge from a food manufacturing plant. Two sequential anaerobic bioreactors are in line subsequent to the influent wet well(s) where the discharge from the food manufacturing is collected.

The flow rate is 0.75 million gallons per day. In the anaerobic bioreactors, the flow from the wet wells is contacted with the composition described in Table III, above. The ratio of the flow of waste water and the composition of Table III varies from 0.0000667% to 0.0002667%. After treatment in the anaerobic zone, the liquid effluent from the bioreactors is led to one or more aeration lagoons for further treatment. The gaseous effluent from the bioreactors is collected and either flared or recycled (and may be treated e.g. to increase its BTU value, prior to recycling) for use in providing heat to the bioreactors and or the food processing boiler used to generate heat steam for the manufacturing process.

It was found that treatment of the influent to the bioreactor with the composition of Table III increases the amount of biogas, i.e. Biomethane, produced. This is a surprising result because the composition of Table III lacks active enzyme. In addition the sludge volume of the effluent is reduced.

Example 2

In a separate example of the process of this invention, the waste water from a large cheese manufacturing plant is treated in an anaerobic digestion zone with the composition of Table III, above, at a ratio of from 0.0220 to 0.1484 composition of Table III influent. The Average residence time in the anaerobic zone is 2.72 to 4.28 Day depended on influent flows. The temperature during said treatment is from about 94 to about 102 degrees F. In this trial, the removal rate of the TCOD is increased. This increase is surprising because the composition of Table III lacks active enzyme.

Example 3

The process of the present invention is also utilized in the treatment of sewage sludge from a municipal source. In this trial the influent to the anaerobic zone of a municipal sewage treating plant is contacted with the composition of Table III, above, at a ratio of 0.0271 to 0.122 ESP Gals/100 gal Primary Feed Sludge and a temperature of 92 To 102° F. This residence time of the mixture of sewage sludge and the final composition in the anaerobic zone is 15 to 18 Days depended on Influent primary feed loading to the anaerobic digester. A typical Municipal Waste Water Treatment Facility processes 1000 gallons per day of wastewater for every person served. Approximately 1.0 cubic foot ($ft^3$) of digester gas is produced by an anaerobic digester per person per day. The heating value of the biogas produced by anaerobic digesters is approximately 600 British thermal units per cubic foot ($Btu/ft^3$).

In the present example, the following results are obtained:
T.S. Removal Rates are increased.
T.V.S. removal rates are increased.
Sludge Volumes are reduced.
Actual production of biogas is increased.

These results are surprising because the composition of Table III lacks active enzyme. The processes described in Examples 1 through 3, above, may be repeated with the Composition of TABLE IV and similar results are obtained.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. For example, while not specifically described herein, the biogas generated from the process of this invention may be used in fuel cell applications.

In addition, the above product comprising a combination of a fermentation supernatant product from a *Saccharomyces cerevisiae* culture and a non-ionic surfactant may be used in any of the processes previously disclosed by one of the present inventors. See U.S. Pat. No. 5,820,758 (deodorizing a body of water); U.S. Pat. No. 5,849,566 (decomposing hydrocarbons); U.S. Pat. No. 5,879,928 (treating municipal and industrial waste water) and U.S. Pat. No. 5,885,950 (cleaning grease traps.)

The Northeast Regional Biomass Program, in conjunction with XENERGY, Inc., has completed a comprehensive study examining the feasibility of utilizing bio-based fuels with stationary fuel cell technologies. The findings show that biomass-based fuel cell systems, from a technical perspective, are capable of providing a source of clean, renewable electricity over the long-term. In addition, fuel cells have proven to be successful in this application, in service around the world at several landfills and wastewater treatment plants (as well as breweries and farms), generating power from the methane gas they produce, and reducing harmful emissions in the process.

Fuel cells have been operated at landfills and wastewater treatment facilities all over the United States and in Asia. For example, Connecticut's Groton Landfill has been producing 600,000 kWh of electricity a year, with a continuous net fuel cell output of 140 kW and UTC Power's (formerly IFC/ ONSI) fuel cell system at the Yonkers wastewater treatment plant in New York, produces over 1.6 million kWh of electricity per year, while releasing only 72 pounds of emissions into the environment. In Portland, Oreg., a fuel cell produces power using anaerobic digester gas from a wastewater facility, which generates 1.5 million kWh of electricity per year, substantially reducing the treatment plant's electricity bills.

Fuel Cell Energy, Inc. (FCE) is installing its Direct FUELCELL® (DFC) power plants at wastewater treatment plans around the world. Both FCE and UTC have installed fuel cells at several breweries—Sierra Nev., Kirin, Asahi and Sapporo—using the methane-like digester gas produced from the effluent from the brewing process to power the fuel cell. The process of the present invention can be used to generate a biogas that may be used in any of the above commercial processes to generate power from waste. It is intended that all such modifications will fall within the scope of the appended claims.

The invention claimed is:

1. A method for treating a contaminated water, the method comprising the step of:
adding a bio-catalytic composition to the contaminated water, the bio-catalytic composition comprises a fermentation supernatant from a yeast culture containing no active enzymes and one or more nonionic surfactants, the fermentation supernatant including bio-nutrients, minerals and amino acids,
wherein addition of the bio-catalytic composition to the contaminated water forms a plurality of microbubbles having a reactive membrane barrier that enhances oxygen or other gas transfer across the reactive membrane barrier.

2. The method according to claim 1, wherein the microbubbles serve as a broad-spectrum facilitator of accelerated biological and chemical reactions in situ.

3. The method according to claim 1, wherein the enhanced oxygen transfer across the reactive membrane barrier effects breaking of ester bonds present in an organic material.

4. The method according to claim 1, wherein the microbubbles increase dissolved oxygen and/or other gas reservoirs.

5. The method according to claim 1, wherein the contaminated water is present in a closed loop water system.

6. The method according to claim 5, wherein treatment of the contaminated water results in an inhibition of biological film growth and a degradation of biologically produced structural biofilms.

7. The method according to claim 1, wherein the contaminated water is present in a pulp and paper mill.

8. The method according to claim 7, wherein treatment of the contaminated water results in a reduction in bacterial and pathogen colony counts, an inhibition of biological film growth, a reduction in starch build-up on rollers, and/or a reduction of spotting on paper.

9. The method according to claim 1, wherein the contaminated water is present in a wastewater treatment plant.

10. The method according to claim 9, wherein treatment of the contaminated water results in an accelerated remediation of organic pollutants, a reduced production of volatile organic compounds and noxious gases, and/or an increase in dissolved oxygen levels.

11. The method according to claim 1, wherein the contaminated water is present in a swimming pool.

12. The method according to claim 11, wherein treatment of the contaminated water results in a reduction of chlorine consumption, a reduction in scaling and/or a reduction in the backwash of settled oxidized residues.

13. The method according to claim 1, wherein the bio-catalytic composition has a pH of about 3.5 to about 4.0.

14. The method according to claim 1, wherein the yeast culture is a *Saccharomyces cerevisiae* culture.

15. The method according to claim 1, wherein the one or more nonionic surfactants comprise a polyether nonionic surfactant, a polyhydroxyl nonionic surfactant, and/or a biosurfactant.

16. The method according to claim 15, wherein the polyhydroxyl nonionic surfactant comprises a sucrose ester, an ethoxylated sucrose ester, a sorbital ester, an ethoxylated sorbital ester, an alkyl glucoside, an ethoxylated alkyl glucoside, a polyglycerol ester, or an ethoxylated polyglycerol ester.

17. The method according to claim 1, wherein the one or more nonionic surfactants comprise an amine oxide, an ethoxylated alcohol, an ethoxylated aliphatic alcohol, an alkylamine, an ethoxylated alkylamine, an ethoxylated alkyl phenol, an alkyl polysaccharide, an ethoxylated alkyl polysaccharide, an ethoxylated fatty acid, an ethoxylated fatty alcohol, an ethoxylated fatty amine, or a nonionic surfactant having the general formula of $H(OCH_2CH_2)_xOC_6H_4R$, $H(OCH_2CH_2)_xOR^1$, or $H(OCH_2CH_2)_xOC(O)R^1$, wherein x represents the number of moles of ethylene oxide added to an alkyl phenol and/or a fatty alcohol or a fatty acid, R represents a long chain alkyl group, and $R^1$ represents a long chain aliphatic group.

18. The method according to claim 17, wherein the long chain alkyl group is a $C_7$-$C_{10}$ normal-alkyl group and/or wherein the long chain aliphatic group is a $C_{12}$-$C_{20}$ aliphatic group.

19. The method according to claim 1, wherein the one or more nonionic surfactants is an ethoxylated nonyl phenol, an ethoxylated octyl phenol, an ethoxylated ceto-oleyl alcohol, an ethoxylated ceto-stearyl alcohol, an ethoxylated decyl alcohol, an ethoxylated dodecyl alcohol, an ethoxylated tridecyl alcohol, or an ethoxylated castor oil.

20. The method according to claim 1, wherein the bio-catalytic composition comprises from about 1% to about 15% by weight of the one or more nonionic surfactants.

* * * * *